United States Patent [19]

Antonetti et al.

[11] Patent Number: 4,980,149

[45] Date of Patent: Dec. 25, 1990

[54] REDUCTION OF THE TOXIC EFFECTS CAUSED BY ANTHRAQUINONE DRUGS

[75] Inventors: Francesco Antonetti; Francesco Borrelli; Fabrizio Martelli, all of Rome, Italy

[73] Assignee: Istituto Fermacologio Serono SpA', Italy

[21] Appl. No.: 763,472

[22] Filed: Aug. 7, 1985

[30] Foreign Application Priority Data

Aug. 9, 1984 [IT] Italy .................................. 48710 A84

[51] Int. Cl.$^5$ ............................................. A61K 49/00
[52] U.S. Cl. ...................................... 424/10; 514/922
[58] Field of Search .................. 424/10, 101; 514/922

[56] References Cited

U.S. PATENT DOCUMENTS 4,529,697 7/1985 Yoshimura et al. ................. 435/110
4,548,927 10/1985 Eaton ..................................... 514/34

OTHER PUBLICATIONS

The Merck Index, Tenth Edition, Publ. by Merck & Co., Inc., 1983, p. 6748 (6742).
Young et al., "The Anthracycline Antineoplastic Drugs", The New England Journal of Medicine, vol. 305, pp. 139-153 (1981).
A. M. Michelson et al., "Superoxide and Superoxide Dismutases", by Menender-Huber, pp. 537-549.

*Primary Examiner*—Douglas W. Robinson
*Attorney, Agent, or Firm*—Ostrolenk, Faber, Gerb & Soffen

[57] ABSTRACT

The toxic effects caused by anthraquinone drugs, particularly by antitumor anthraquinone drugs, are inhibited or reduced by administering Orgotein in a quantity sufficient to inhibit or reduce the superoxide radicals which are produced by the above mentioned drugs.

5 Claims, 2 Drawing Sheets

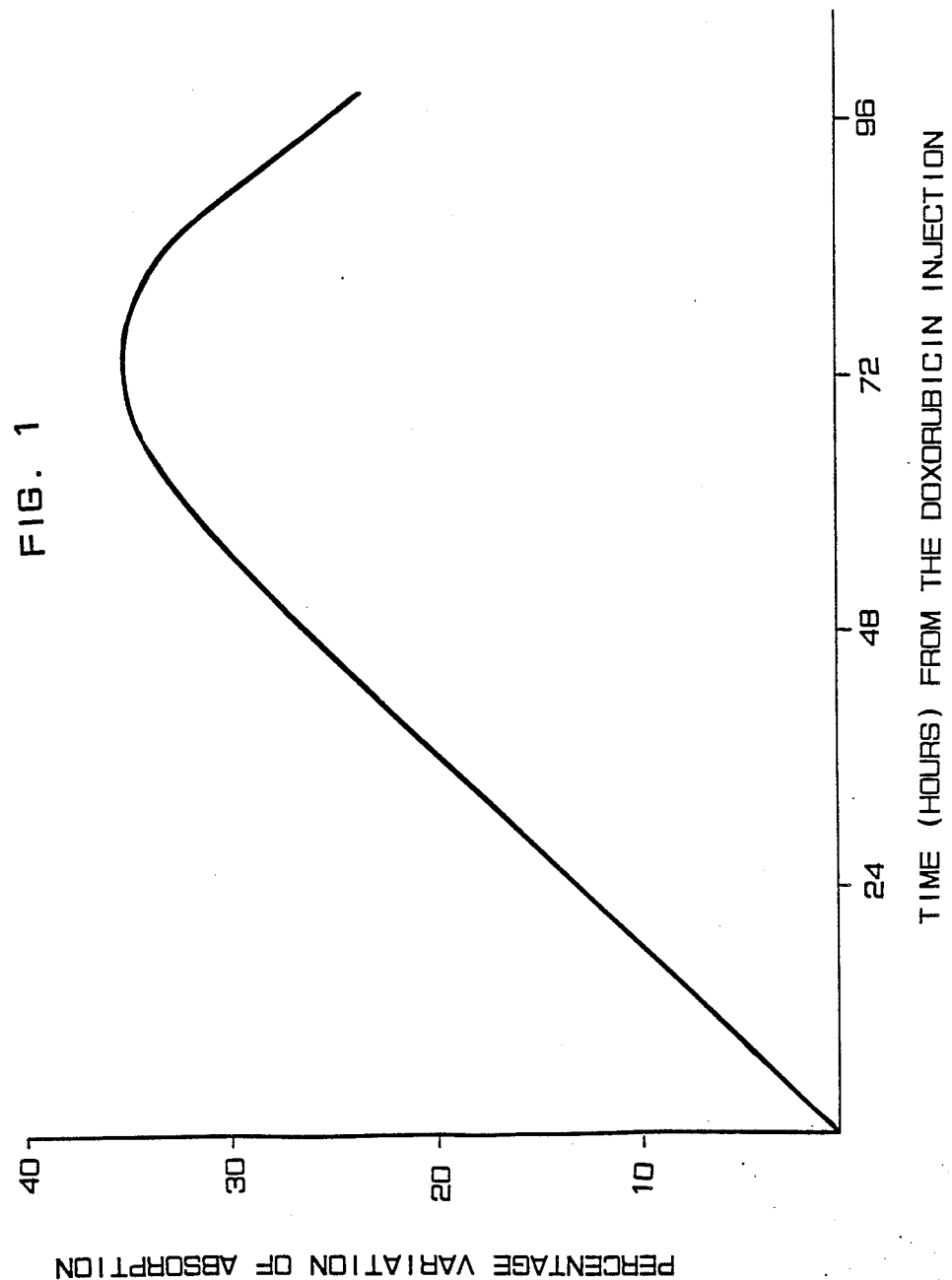

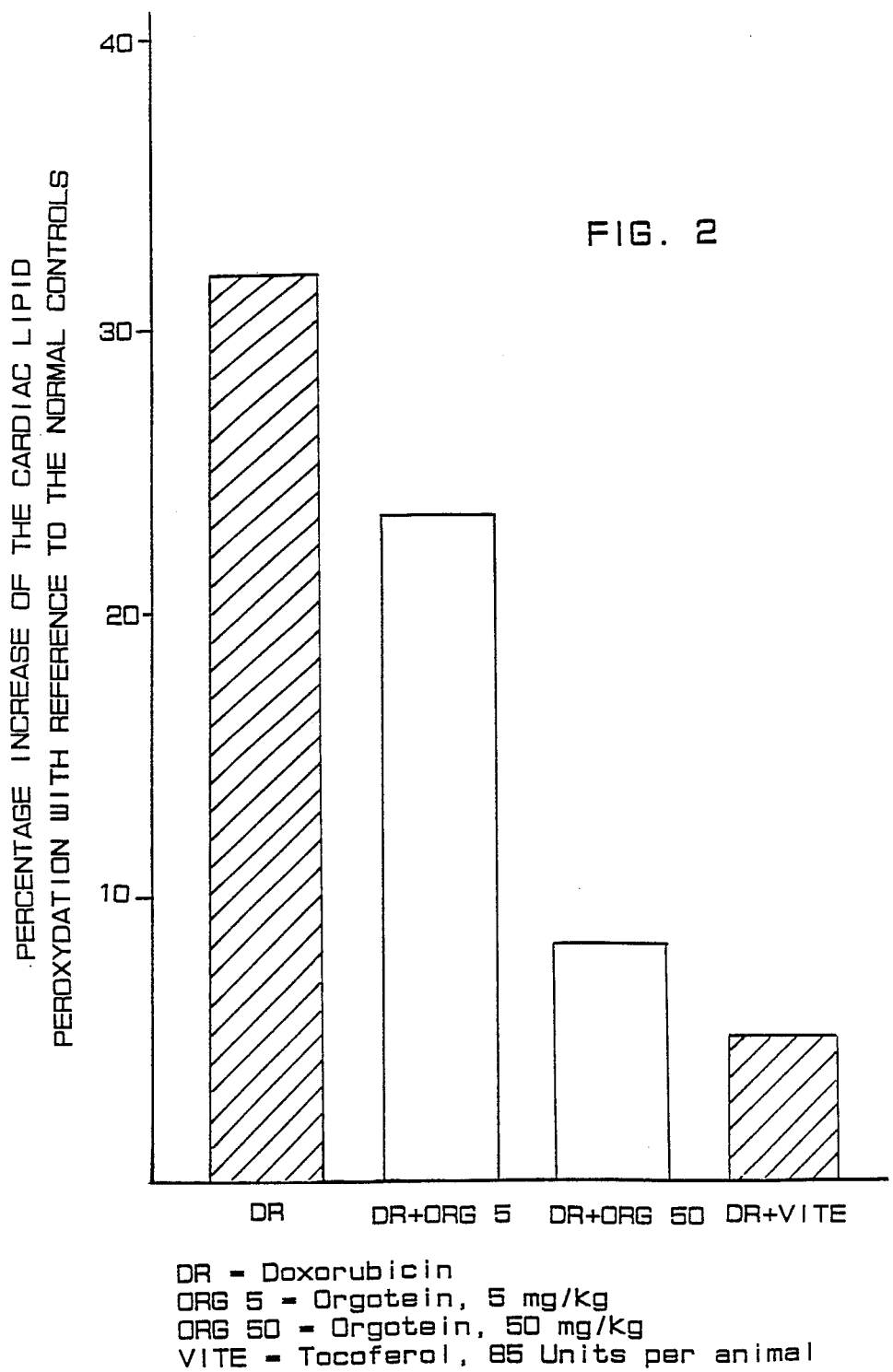

REDUCTION OF THE TOXIC EFFECTS CAUSED BY ANTHRAQUINONE DRUGS

This invention concerns the use of Orgotein in order to reduce the toxic effects caused by anthraquinone drugs. Orgotein is a metal-protein, containing copper and zinc, which can be extracted from blood cells and from various tissues of a number of mammal species. It belongs to the class of enzymes having a superoxide-dismutase activity, being physiologically responsible for the elimination of the $O_2^-$ radicals which are produced during the cellular respiration, and which are detrimental for the organism.

the presence of superoxide radicals in the extracellular fluids may be considered abnormal, and indeed, if they are not rapidly eliminated, they can cause in the exposed tissues several very serious damages with pathological events of various types.

Recent investigations have shown that an abnormal production of superoxide radicals occurs with reference to various types of inflammations.

Controlled investigations made on patients suffering from arthritic diseases, both of a chronic and of a degenerative kind (rheumatoid arthritis, osteoarthrosis) have shown that Orgotein, administered via intramuscular, intraarticular or periarticular injection develops a powerful anti-inflammatory action, because it is able to eliminate the superoxide radicals present at the level of the articulations suffering from the above mentioned diseases thus interrupting one of the pathogenetic moments supporting these diseases.

The biochemical studies have clarified the mechanism of action by which the enzymes having a superoxide-dimutase activity, and in particular Orgotein, eliminate the harmful superoxide radical from the extracellular fluids.

The principal reaction is one of dismutation where the above mentioned enzymes perform a catalytic action, which transforms the superoxide radical into molecular oxygen and hydrogen peroxide:

$$O_2^- + O_2^- + 2H^+ \rightarrow O_2 + H_2O_2$$

One of the most efficient and well known chemiotherapic agents for the treatment of cancer is Doxorubicin, an anthraquinone antitumor drug. It results to be the most efficacious agent in the treatment of mammary cancer and of other sarcomas of the soft tissues and furthermore has a considerable activity in the treatment of solid tumors.

Unfortunately, the use of Doxorubicin and of other anthraquinone antitumor drugs is strongly restricted by its collateral effects, which are particularly evident at cardiac level. In the specific case of Doxorubicin, its collateral effects are characterized by a chronic, dose-dependent myocardiopathy. Such a collateral effect which could eventually bring about a sudden and irreversible collapse of the cardiac muscle, presents serious problems, thus limiting the use of this drug in tumor therapy.

The experiments which resulted in the present invention were based upon the hypothesis that the mechanism of action for such a serious collateral effect by Doxorubicin may be due to lipidic peroxidation started by the forming of free radicals. In fact, the quinonic structure of Doxorubicin is electrically unstable and may be converted into semi-quinonic free radicals, with the consequent production of superoxide anions. These anions, in turn, may start some chain reactions mediated by free radicals, which bring about in the last analysis, a transformation of unsaturated membrane fatty acids into peroxidized lipids.

The main aim of the present consists in providing a method for the reduction of toxic effects caused by anthraquinone drugs, in particular antitumour anthraquinone drugs, which is based on the concomitant administration of Orgotein in a quantity sufficient to inhibit or reduce the superoxide radicals produced by the above mentioned drugs. The invention will be more completely illustrated by means of the following examples, where the determination of the toxic effect caused by anthraquinone drugs has been assessed by means of the determination assay of the cardiac lipoperoxide content according to Uchiyama and Mihara (Analytical Biochemistry 86:271-278, 1978) based upon the spectrophotometric measurement (535 nm-520 nm) of the reaction complex with thiobarbituric acid, performed on the homogenate of cardiac muscle. In order to exclude all possible interference with the lipoperoxide determination assay, some known quantities of malonic dialdehyde were added to added to five samples of cardiac muscle homogenate, and the recovery of the dialdehyde was determined by means of a standard curve obtained with the same analytical process.

EXAMPLE 1

40 Male mice $CD_1$-COBS (Charles River) weighting $20\pm2$ g were treated with a single intravenous Doxorubicin (7.5 mg/kg) injection. At 24, 48, 72 and 96 hours after the injection, the animals were sacrificed (in groups of ten at a time) and their cardiac muscles immediately removed, weighted and treated to perform the above described test. A control group of a further ten mice received physiological solution only.

Results are shown in FIG. 1, from which it may be seen that the administration of 7.5 mg/kg Doxorubicin by the intravenous route provokes an increase of cardiac lipoperoxidation reaching a maximum after 72 hours.

EXAMPLE 2

In this example, five groups of mice $CD_1COBS$ (Charles River) weighing $18\pm1$ g were used: each group consisted of 17 animals. Of the treated groups, four received Doxorubicin at the dosage of 7.5 mg/kg by the intravenous route. The first two groups of the four groups treated also received Orgotein in quantities of 5 and 50 mg/kg respectively subcutaneously whereas the other two groups received: the first group 85 Units per mouse Tocoferol via the intraperitoneal route and the second group received physiological solution subcutaneously.

The fifth group was used as a normal control and received physiological solution only.

Administration times for Tocoferol and Orgotein were as follows: Orgotein was administered daily, starting from 72 hours before, and ending 72 hours after the administration of Doxorubicin: Tocoferol was administered once only, 24 hours before the Doxorobucin injection.

The animals were sacrificed 72 hours after the administration of Doxorubicin and their cardiac muscles immediately removed, weighed and treated in order to perform the above described test.

FIG. 2 illustrates the results of this test, which confirm that Doxorubicin induced an increase of the lipid peroxidation with respect to the untreated control mice, whereas the administration of Orgotein, in dosages of 5 and 50 mg/kg caused a decrease in the increment of lipid peroxidation levels. The effect obtained with the higher dosage of Orgotein is comparable to that obtained with Tocoferol, which was used as reference drug.

From the results of the above described experiment, it may be deduced that the use of Orgotein is advantageous for protection against the cardiotoxic effects caused by Doxorubicin and other anthraquinone drugs used in the treatment of tumors.

We claim:

1. A method for reducing myocardiopathy caused by the administration of an anthraquinone antitumor drug which comprises administering an effective cardiotoxic reducing amount of orgotein.
2. The method of claim 1 wherein the administration of orgotein is effected subcutaneously.
3. The method of claim 1 wherein the administration of orgotein is effected concomitantly with the administration of the anthraquinone antitumor drug.
4. The method of claim 1 wherein the anthraquinone antitumor drug is doxorubicin.
5. The method of claim 4 wherein the administration of orgotein is effected subcutaneously and concomitantly with the administration of the doxorubicin.

* * * * *